US009516944B2

(12) United States Patent
Lawrence

(10) Patent No.: US 9,516,944 B2
(45) Date of Patent: Dec. 13, 2016

(54) STERILIZABLE PLATFORM WITH CONFIGURABLE FRAME AND METHOD OF CONSTRUCTING

(71) Applicant: Steven Lawrence, Sheboygan, WI (US)

(72) Inventor: Steven Lawrence, Sheboygan, WI (US)

(*) Notice: Subject to any disclaimer, the term of this patent is extended or adjusted under 35 U.S.C. 154(b) by 0 days.

(21) Appl. No.: 14/573,876

(22) Filed: Dec. 17, 2014

(65) Prior Publication Data

US 2015/0320199 A1    Nov. 12, 2015

Related U.S. Application Data

(60) Provisional application No. 61/994,639, filed on May 16, 2014.

(51) Int. Cl.

| | |
|---|---|
| *A47B 47/04* | (2006.01) |
| *A47B 13/06* | (2006.01) |
| *C12C 11/00* | (2006.01) |
| *C12C 13/10* | (2006.01) |
| *B21D 47/04* | (2006.01) |
| *A47B 7/00* | (2006.01) |
| *E04B 1/24* | (2006.01) |
| *E04C 3/04* | (2006.01) |
| *B01L 9/02* | (2006.01) |
| *A47B 37/00* | (2006.01) |
| *A61B 17/00* | (2006.01) |

(52) U.S. Cl.
CPC ............. *A47B 13/06* (2013.01); *A47B 47/047* (2013.01); *A61B 50/10* (2016.02); *A61B 50/15* (2016.02); *B21D 47/04* (2013.01); *C12C 11/006* (2013.01); *C12C 13/10* (2013.01); *A47B 7/00* (2013.01); *A47B 2037/005* (2013.01); *A61B 2017/00526* (2013.01); *B01L 9/02* (2013.01); *E04B 2001/2415* (2013.01); *E04B 2001/2472* (2013.01); *E04C 2003/0413* (2013.01); *Y10T 403/479* (2015.01)

(58) Field of Classification Search
CPC ......... A47B 13/06; A47B 7/00; A47B 47/047; A47B 47/05; B21D 47/01; B21D 47/04; E04C 3/07; E04C 2003/0413; E04C 2003/0434; E04C 2003/0417; E04C 2003/0452; E04B 2001/2415; E04B 2001/2463; E04B 2001/2472
USPC ........ 248/188.1; 52/840, 836, 837, 838, 839
See application file for complete search history.

(56) References Cited

U.S. PATENT DOCUMENTS

| | | | | |
|---|---|---|---|---|
| 3,241,885 | A * | 3/1966 | Deaton | A47B 47/047 108/186 |
| 4,126,364 | A * | 11/1978 | Reilly | F16B 12/50 312/140 |
| 4,232,845 | A * | 11/1980 | Turner | F16L 3/26 174/101 |

(Continued)

*Primary Examiner* — Anita M King
(74) *Attorney, Agent, or Firm* — Mandy T. Garrels; Ceres Patent & Technology, LLC

(57) ABSTRACT

A free standing self sterilizable device and method of construction by connecting together a plurality of connected individual modular components. The individual modular components are provided in such manner to enable multiple configurations in frame structure shape when assembled. The device is self sterilizing by its material composition, its open smooth surface and its downward or horizontal slanting surfaces. The device herein is intended for use in the food or medical industry.

9 Claims, 4 Drawing Sheets

(56) References Cited

U.S. PATENT DOCUMENTS

| | | | | |
|---|---|---|---|---|
| 4,693,524 A | * | 9/1987 | Navarro | A47B 47/05 108/159 |
| 8,468,774 B2 | * | 6/2013 | Garry | B21D 47/01 52/836 |
| 8,573,409 B2 | * | 11/2013 | White | H02G 3/0608 108/64 |
| 2007/0163980 A1 | * | 7/2007 | Gonzalez Llorens | A47B 47/021 211/189 |

* cited by examiner

STERILIZABLE PLATFORM WITH CONFIGURABLE FRAME AND METHOD OF CONSTRUCTING

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

CROSS REFERENCE

This non-provisional utility patent application incorporates by reference the earlier filed provisional patent application, Application No. 61/994,639, in its entirety. This non-provisional patent application claims benefit of said copending provisional patent application, effectively filed on May 16, 2014, pursuant to 35 U.S.C. 119(e) and 37 C.F.R. 1.78 (a)(4)-(a)(6) and all other relevant sections of the law not referred to herein.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark office, patent file or records, but otherwise reserves all copyright rights whatsoever.

BACKGROUND OF THE INVENTION

Field of the Invention

The present matter relates to a sterilizable platform with supporting frame and method of construction, specifically pertaining to counters and supporting counter frames used in the preparation of food products or medical related products subject to strict standards for sterility.

Background

Federal regulation over the manufacture of products within certain industries, such as food or medical related products, are subject to strict sterile guidelines. Particularly within the food industry, instruments and platforms in direct contact with food material must undergo regular sterilization between periods of use to ensure a healthy result for end consumption. In some cases as with medical equipment, the final product itself must achieve sterility, further raising the bar for the need to effectively and efficiently maintain a sterile manufacturing environment.

The challenge in meeting these standards is with the balance of cost. A majority of manufacturers producing food or medical products typically contract through secondary manufacturers for their equipment needs. A cheese manufacturer may require a length of stainless steel table for assembly line processing. Federal regulations currently require the processing area, including any material contact with the food product during processing, to be regularly washed and sterilized. Therefore, an entire length of table platform would have to undergo washing or sterilization, a time consuming endeavor if involving spare parts. Any area where a seam is open or where crevices exist such that bacteria may collect would have to be removed for separate thorough cleaning. In some cases, entire sections of area would have to shut down daily, costing a great deal in labor and expense. The period of usability after sterile cleaning will vary depending on the style of design of the equipment and the product in contact with it. In the food industry, particularly with cheese manufacturing, the period of usability before the next cycle of maintenance of a standard processing table can be a 12 hour period. Given the low demand and high variability in design requirements (for the specific needs of each particular industry and company), suppliers and manufacturers of these equipment respond to custom demands. As such, no generic or standard sterilizable table or support equipment exists at this time. From both economical and practical points of view, the custom needs of each company and industry makes it very difficult to establish a standard product appealable to the large inconsistent market.

The common scenario at this time involves purchase of standard nonsterilizable tables which are then customized to fit sterile needs. Standard nonsterilizable tables are more accessible in the market. The components of such tables typically have legs that are hollow tubes screwed onto the bottom surface of a table top. The bottom end of the tubing is capped to soften its impact on the ground surface and to close out the hollow space of the legs. The interconnection is often achieved by nonwelding methods such as by screw, tension or adhesive means. For purposes of customizing the product for sterilizable use, they are often brought into a secondary manufacturer to weld the seam edges. However, the prefabricated tables being manufactured with different specifications not intended originally for welding purposes often crack and break at their secondary welds or due to physical imbalance caused by the welding. The weld that reinforces or adds to strength at certain areas of the table may highlight other portions that are naturally weaker, particularly under heavy use. Unless a piece of equipment is engineered to meet certain types of conditions, jerry-rigging an imperfect product to meet unexpected demands does not provide effective solution. Such damages result in expensive liability and noncurable defects to the entire device or large portions of the device within proximity to the defective portions. This is a continuous problem in the industry.

SUMMARY OF INVENTION

Figure 1:
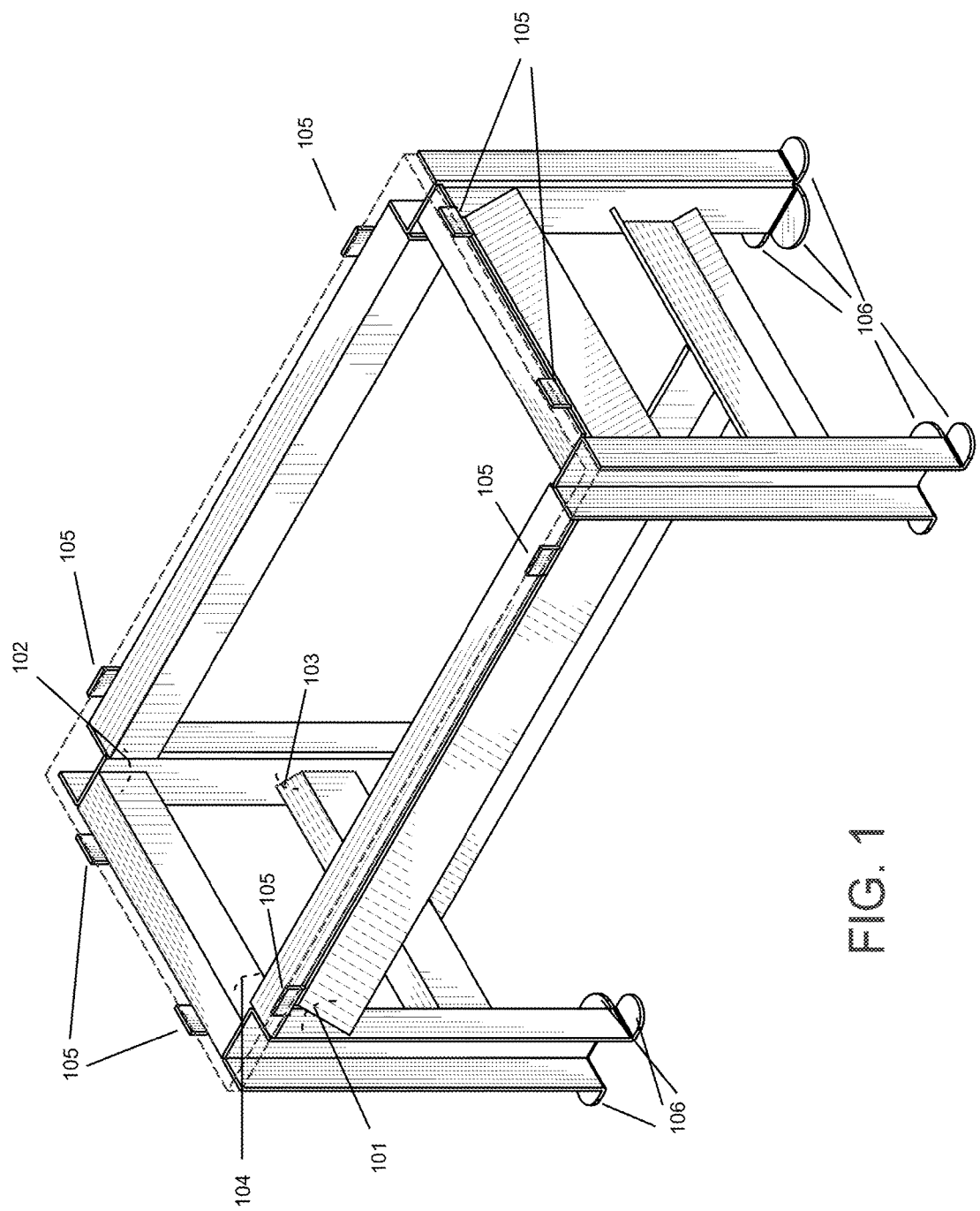
FIG. 1 is a side perspective view of a preferred embodiment of the invention disclosed herein.

The invention herein is directed to a device comprising a sterilizable support frame or platform and a system of constructing said device comprising intersecting preconfigured components. The device is drawn to any variety of embodiments wherein each embodiment is composed of joined intersecting preconfigured components of this invention. The preconfigured components are permanently and seamlessly intersected and joined together according to their matching features. The device is comprised of sterile grade sterilizable solid durable material. The engineered shape of the final construct and its separate components when assembled should enable easy sterile cleaning, greater assurance against contamination and elimination of the need to remove connected parts. The improvement comes from successfully eliminating attachments and hollow or grooved hidden areas where bacteria may collect. Any variety of support frame shape or design may be constructed from this system. The invention here provides for separate components that when assembled in a desired manner, provides a device platform or support frame with continuous open surfaces that slant at a downward angle, facilitating a natural flow and removal of debris by gravitational pull. There is no surface on this device where debris or material may be trapped, requiring manual cleaning. The engineered design of each separate component is configured to be joinable in flush manner with each other to form a variety of devices with various shapes that have in common said open and downward angled surfaces. The components are permanently joined in seamless manner to create a fluid contiguous connection of multiple surfaces with no hidden or open crevices where bacteria may otherwise collect. The connections may be welded, bonded, molded, or by any otherwise known method for permanent fusing the material together to create a fluid and seamless connection. The points of connection or attachment between the separate device components are permanent in nature.

The preconfigured components may be joined to form a variety of embodiments. Each component is a length of flat material having a straight, angled or rounded surface and is cut or joined at its cross section. The cross sectional shape of each component may be welded (or permanently connectable in seamless manner) to another component surface to create a seamless connection with no hidden surface. The shape and surface of the component when configured in its final embodiment should angle downward to allow unobstructed dripping and gravity pull on debris or material attached thereon.

Each component and its cross sectional shape should have the following qualities in common: 1) may be welded or permanently attachable to another component with seamless interconnection, 2) have no hollow or hidden surfaces where debris may collect, 3) the surface of each component having a length, width and thickness, 4) the cross section of each component comprising a flat, rounded or sharp angled shape, 5) the ends of each matching component contacting each other in flush manner. The preferred cross sectional angle should comprise any of the following: 180 degree, 135 degree, 90 degree or 45 degree angles. These components may be manufactured as separate standard preconfigured parts and sold in quantity for custom building of a desired sterile grade product. Alternatively, the device may be sold in constructed form. The choice of embodiment of the device depends on the user's preferences.

Every protrusion that extends from the surface of a component should be a continuous piece of the material forming the component. That protrusion extending from the surface edge of the component may be bent at an angle to serve a particular secondary purpose such as providing additional support or softening contact. In any case, no additional welding is necessary with regards to support protrusions or tabs. Said tabs located at the bottom of a component serving as a table leg may be bent to provide a smooth rounded surface to soften impact on the floor surface. This is an acceptable substitute for padding typically glued or screwed onto the bottom of a table leg to minimize scuffing of floor surfaces. Alternatively, the protrusions or tabs may extend upward from a horizontal frame to hold material inward within the constructed support frame device.

Several embodiments of this invention have been constructed according to the separately claimed and described components herein. These embodiments, particular two pertaining to a table support frame and a table frame and platform, both with tab support, have been reviewed by the USDA and certified according to their assembled form.

DETAILED DESCRIPTION

Figure 4:
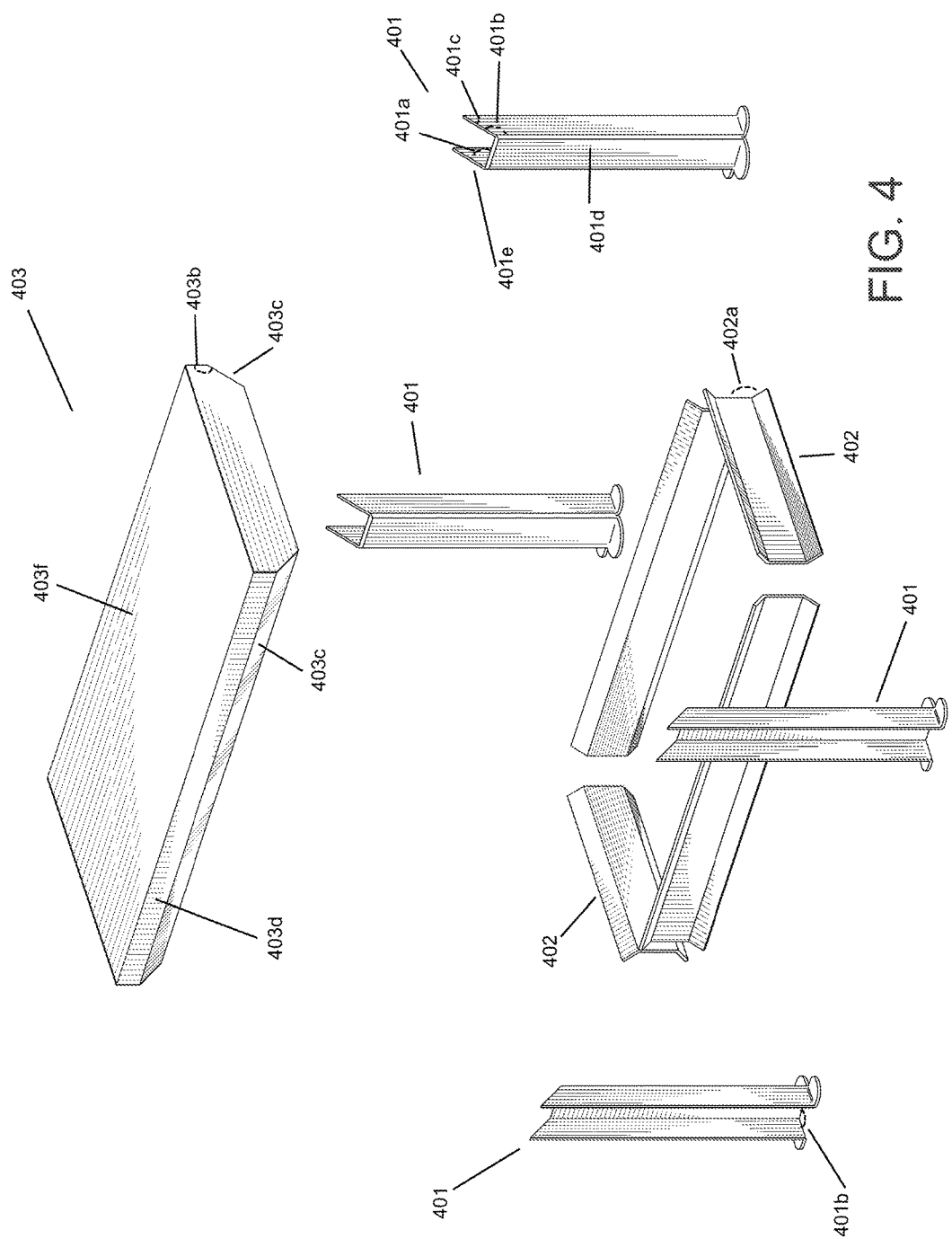
FIG. 4 is a perspective view of the separate components comprising a preferred embodiment of the invention disclosed herein, specifically relating to the design of FIG. 3.

Each component (FIG. 2, 201, 202, 203, 204; FIG. 4, 401, 402, 403) comprising solid sterilizable material, preferably made of durable stainless metallic material that may be bent and welded. Each said component further having a length, a width, a thickness, and a cross sectional shape. Said cross sectional shape is preferably unchanged throughout the length of each individual said component. Said cross sectional shape of each individual said component having one or more bent angles (FIG. 2, 201*a*, 202*a*, 204*a*; FIG. 4, 401*a*, 401*b*, 402*a*). Each individual of said one or more bent angles comprising any one or more of the following angles of bending: 180 degree, 135 degree, 90 degree or 45 degree angles. Each said component having two or more ends (FIG. 2, 201*b*, 201*c*, 202*b*, 202*c*, 203 *a*, 203*b*, 204 *b*, 204*e*). Each said end being cut at either a 45, 90 or 135 degree angle (FIG. 2, 201*d*, 204*d*; FIG. 4, 401*b*, 401*c*) to enable welding against the surface of another component to create an open surface between the connected components at their location of weld with an angle of 180, 135, 90 or 45 degree angles (FIG. 3, 301, 302, 303, 304, 305; FIG. 1, 101, 102, 103, 104).

Each component and its cross sectional shape should have the following qualities in common: 1) may be welded or permanently attachable to another component with seamless interconnection, 2) have no hollow or hidden surfaces where debris may collect, 3) the surface of each component having a length, width and thickness, 4) the cross sectional shape of each component comprising a flat, rounded or sharp angled shape, 5) the ends of each matching component contacting the surface of another component in flush manner. The preferred cross sectional angle of cut should comprise factors of 45 degree angles, including any of the following: 180 degree, 135 degree, 90 degree or 45 degree angles. These components may be manufactured as separate standard preconfigured parts (see FIGS. 2 and 4) and sold in quantity for custom building of a desired sterile grade product. Alternatively, the device may be sold in constructed form (see FIGS. 1 and 3). The choice of embodiment of the device depends on the user's preferences.

Figure 2:
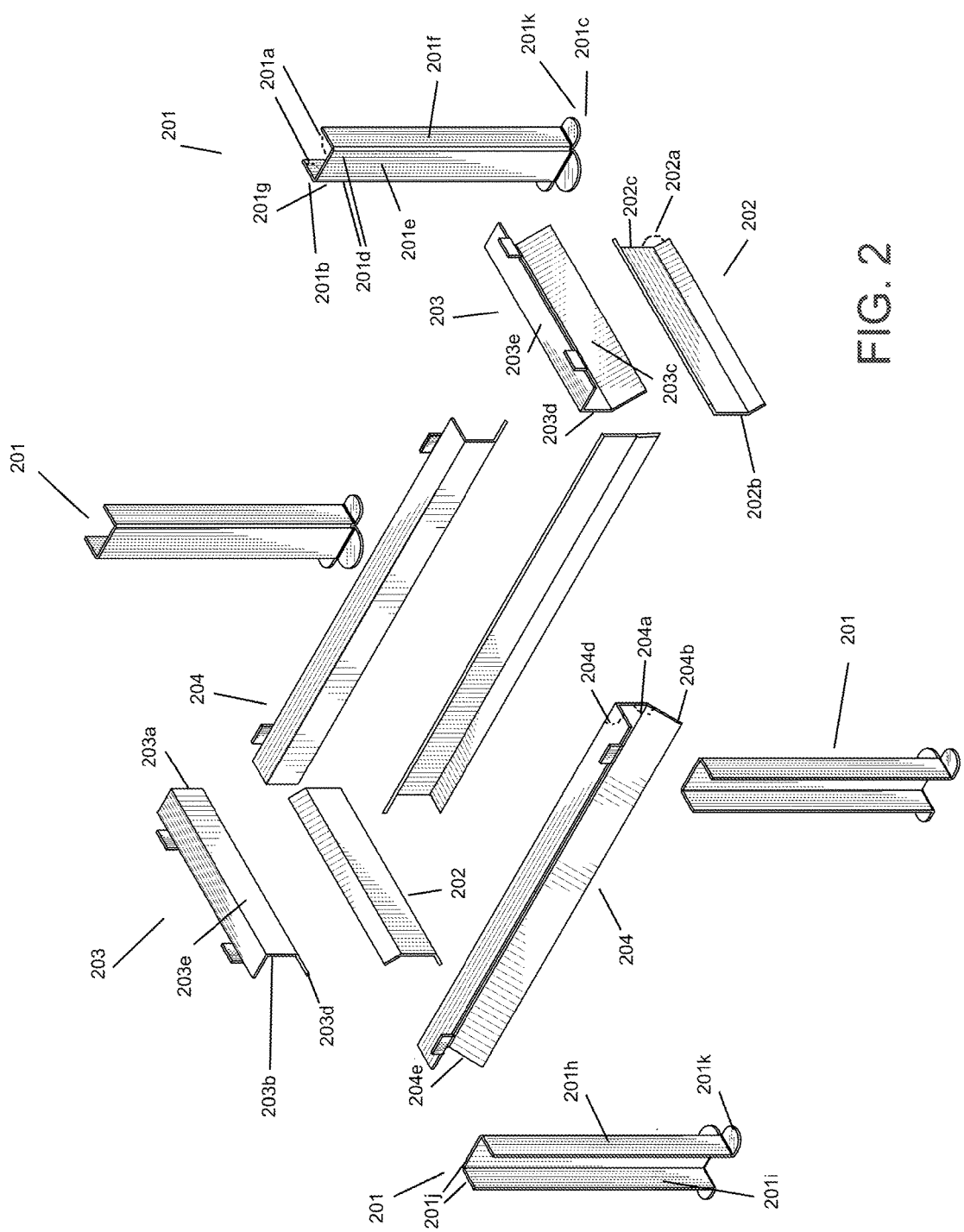
FIG. 2 is a perspective view of the separate components comprising a preferred embodiment of the invention disclosed herein, specifically relating to the design of FIG. 1.
Figure 3:
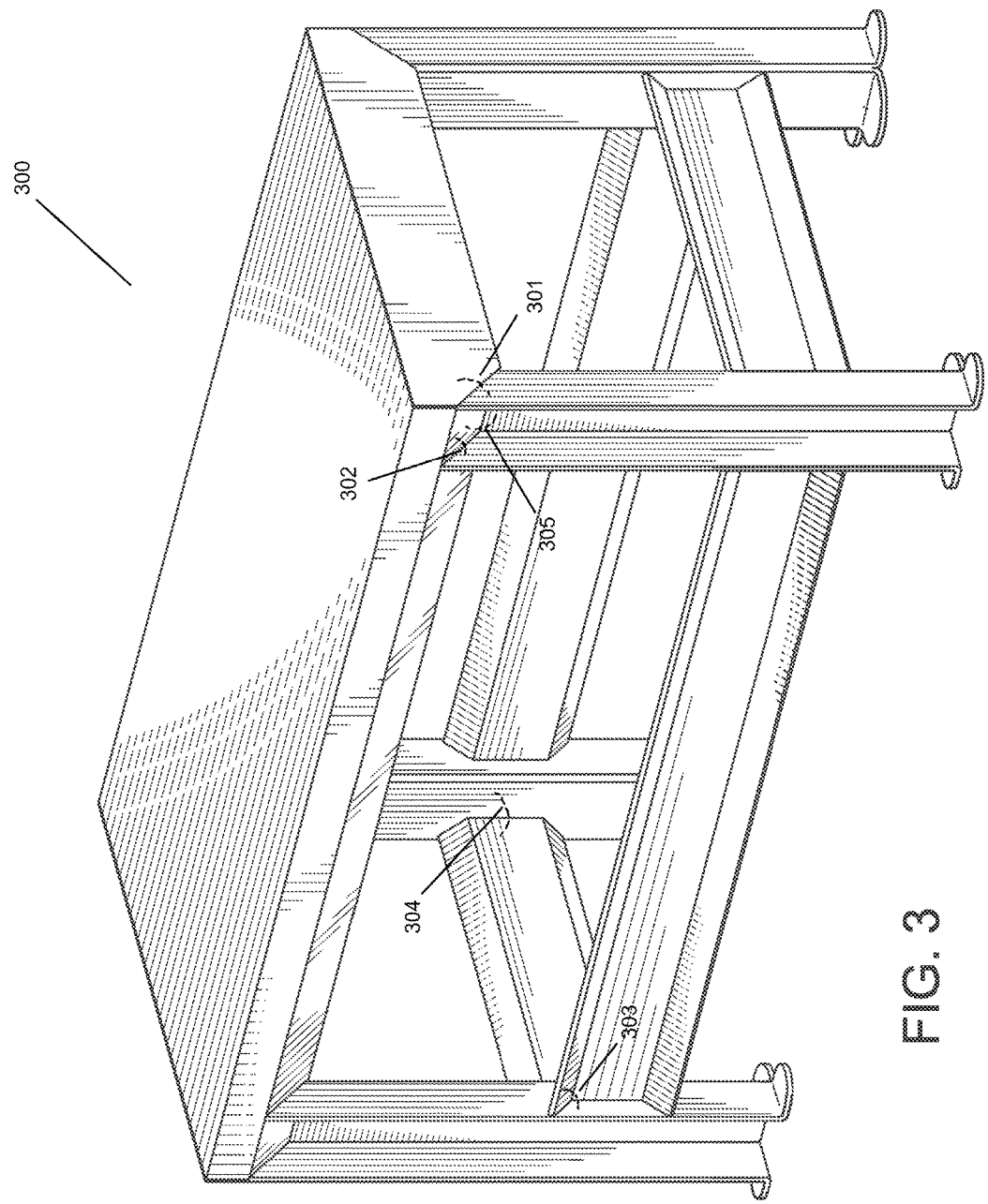
FIG. 3 is a side perspective view of a preferred embodiment of the invention disclosed herein.

According to a first preferred embodiment FIGS. 1 and 2 of this invention, the cross section of a first component 201 comprises three elements with long planar surfaces. A first planar element 201*e* designated as a central piece and the remaining two elements, 201*f* and 201*g*, designated as side pieces extending from either ends of the central piece at perpendicular angles. The three elements may comprise a single planar piece of material bent at two sides to create the desired cross sectional shape or alternatively three separate elements permanently connected along the length of their side edges. The cross section provides an angular U shape with perpendicular corners 201*a* where the pieces intersect. The angular U shape defining the open cross sectional design allows cleanser and cleaning equipment to fully access the entire surface of the component without need for removal of parts for additional access. The entire surface of said component would be completely exposed to the ambient environment according to this open cross sectional design. The first embodiment is intended to rest on the ground surface at one end 201c, 201k along its cross sectional plane, serving a primary affect of a leg piece for a standing product. Each of the three elements have a front 201h, back 201i and side edge 201j (defined by the thickness of the material) surface that when interconnected in the manner of this embodiment, provides for open surfaces all around with no hidden or hollow grooves where debris may collect. Both first 201b and second ends 201c may be cross cut horizontally providing a flat cross sectional surface for flush parallel or perpendicular contact with another planar surface. With this type of cut, either ends may rest vertically and perpendicularly on a ground surface. The surface of this first embodiment being vertically and perpendicularly positioned 201k to the ground allows gravitational movement downward of material attached thereon. This facilitates self cleaning without need for mechanical efforts to remove debris. A combination of high pressure hot water spray and air drying would be sufficient to achieve sterility as a means of self cleaning. With no hidden crevices, hand scrubbing or need for removal of parts would be necessary to ensure sterile quality in cleaning. The first or second end of this first component (when all three elements are interconnected in the manner described above) may be cut at an angle 401b, 401c to allow flush contact with another planar surface 403c having an angular cross sectional shape 403b. This change in the angle of cut would comprise a second alternative embodiment 401, 300, providing yet another configuration to broaden the options of products.

The greater purpose of this invention is to provide modular components that can be interconnected in a variety of ways to create a stable sterilizable support frame. To effectuate this purpose and accommodate the variety of known predictable types of usage, mostly industrial and commercial in nature, the preferred cross sectional angles should comprise any of the following: 180 degree, 135 degree, 90 degree or 45 degree inward bent angles. If the angles of slant and angles of cut for planar surfaces are based on a common factor of 45 degree, the combination of these components with any of these angles would create a final product with angles of 180, 135, 90 or 45 degree slants, ideal for facilitating downward sliding or dripping movement and the overall purpose of the invention.

This principal may be applied to other configurations of components in this modular system. For example, horizontally positioned components 204, 203, 402, 403 should preferably have surfaces positioned in an upright manner. The intention would be to create a horizontal frame component with vertical or downward angled side surfaces that allow debris to slide downward with the pull of gravity. The cross sectional shape of the horizontal component should dictate surfaces (front 203c, back 203d and side edge surfaces 203e) that direct downward movement of debris towards the ground. The surfaces should not be angled in an upward manner (beyond 180 degree angle or above horizontal) where debris may be caught and trapped nearby. The particular cross sectional shape of the horizontal component 203, 204, 403, 402 would depend on the shape and cut of the vertical components 401, 201 or vice versa. The contact between a horizontally and a vertically positioned component should result in a flush contact, with no hidden grooves, or resulting crevices between surfaces where debris may be trapped. Therefore, the exposed flat surface of a first component (for example, FIG. 4 403c) may attach to an exposed surface of a second component (for example, a side edge surface of the vertical component 401 of FIG. 4) to create a clean planar surface and downward angled structure. The point of attachment or connection should be weldable should not result in grooved or hollow space.

A product or device comprising four vertically positioned components of the first embodiment 101 attached to four horizontally positioned components may create a table like frame structure. The surface of the vertically positioned component would be welded to a side edge surface of horizontal component to create an L bracket. The interconnection of four horizontally positioned components to four vertically positioned components in this manner results in a table frame having four vertical legs and a centrally open frame surface to support and hold a floating tabletop therein. When the table top is removed and the table frame of this example is flipped upside down for washing and drying, all surfaces of the device would face downward to allow drip by gravitational force.

Space conservation may be a secondary consideration in the design of either vertical or horizontal positioned components. For example, an alternate device 300 comprising a table structure providing a permanent table top 403 may comprise components that, when interconnected, should minimize spatial footprint while maximizing usable surface space. In this case, the vertically positioned components of this alternate embodiment 300 would be cut at 45 degree downward angle 401c from the side edge surfaces 401e towards the central element 401d, the central element 401d having a length shorter than the side surfaces. The horizontally positioned component would have central planar element 403f wherein the surface of the central planar element is horizontal and planar, a bent vertical surface 403d extending at the lower edge of the central element by 90 degrees and a slanted lower surface 403c extending below the bent vertical surface 403d at 135 degrees. The slanted lower surface 403d would match the 45 degree cross sectional cut 401c of the leg component 401 flush weldable connection. Since the slanted lower surface 403d extends inward from the bent vertical surface 403d, its attachment to the leg component 401 would result in vertical legs recessed within and under the perimeter of the table top. By welding the matching angles between the leg component 401 and the slanted lower surface 403c, the 45 degree cross section of the leg component 401 is partially capped with an exposed surface that slants downward, allowing dripping to occur and without hidden crevices or hollow surfaces. The table, when washed and dried in its upright position, would be self cleaning since all surfaces are slanted and angled downward with no hidden or isolated space or crevices.

Support tabs 105, 106 may be added at the edges of any surface on the device or individual components. The tabs simply comprise of extra piece of material extending from the edge of any particular surface in a fingerlike manner, and thereafter bent at a perpendicular angle to create a raised edge affect 105 for holding items place. Alternatively, the tabs may extend from the bottom end of the vertical component and bent outward to provide a curved soft edge 106 at the cross section where the vertical component rests against the floor surface. The curved edge 106 softens the contact and minimizes injury to the floor surface with weight and movement between the contact of the table and the floor. The outward extensions serve as a stabilizing element.

Having fully described at least one embodiment of the present invention, other equivalent the invention has been described by way of summary, detailed description and illustration. The specific embodiments disclosed in the above drawings are not intended to be limiting. Implementations of the present invention with various different configurations are contemplated as within the scope of the present invention. The invention is thus to cover all modifications, equivalents, and alternatives falling within the spirit and scope of the following claims. Other features, advantages, and object of the present invention will become more apparent and be more readily understood from the following detailed description, which should be read in conjunction with the accompanying drawings.

Reference will now be made in detail to exemplary aspects of the present invention which are illustrated in the accompanying drawings. Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure, or manner.

It is to be understood that any exact measurements/dimensions or particular construction material indicated herein are solely provided as examples of suitable configurations and are not intended to be limiting in any way. Depending on the needs of the particular application, those skilled in the art will readily recognize, in light of the following teachings, a multiplicity of suitable alternative implementation details.

I claim the following invention:

1. A plurality of modular components for forming a self sterilizable frame structure, wherein
   each individual modular component of said plurality of modular components comprising flat planar nonporous material having a front surface and back surface,
   each said individual modular component of said plurality of modular components having a length wherein said length terminates at a first end and a second end,
   each said individual modular component of said plurality of modular components having a cross sectional shape defined by one or more bends along and parallel to its said length, each said bend comprising an angle starting from 45 degrees to 90 degrees,
   each said first end and second end terminating relative to its said length at a 45 degree or 90 degree cross sectional slant,
   said front and back surfaces of each individual modular component having no overlap, crevices, hollow space, cracks, or such space wherein debris may be isolated or trapped,
   each said individual modular component connectable to another said individual modular component at their respective first or second ends to form an angular connection, said angular connection having an angle starting at 90 degrees and up to 180 degrees,
   each said individual modular component connectable to another individual modular component between said first or second end by seamless connection without overlap between their respective connecting surfaces,
   a plurality of said individual modular components connectable at their respective first and second ends to form a free standing frame structure,
   said front and back surfaces of each individual modular component in connected form of said free standing frame structure is horizontal or downward angled.

2. The plurality of modular components of claim 1 wherein each of said modular components has one or more support tabs, said one or more support tab comprising material that coextends from the material of said length of each said individual modular component, said one or more support tab extending perpendicularly from said first or second ends of said length of each said individual modular component and terminating with round edges.

3. A method of constructing a modular a self sterilizable free standing frame structure from a plurality of individual modular components of claim 1 wherein
   said first or second end of a first individual modular component connecting to a first or second end an exposed surface of a second individual modular component to form an angular connection,
   said connection between said first and second individual modular components being seamless,
   a plurality of three or more of said individual modular components connecting at their respective first and second ends to form a free standing frame structure, and
   said free standing frame structure comprising a self sterilizable surface wherein said front and back surfaces of each individual modular component of said plurality of individual modular component in connected form is horizontal or downward slanting.

4. The method of constructing a modular self sterilizable free standing frame structure according to claim 3, further providing a self sterilizable support tab wherein said flat planar material of each individual modular component extending coextensively at a right angle from its respective length forming one or more self sterilizable support tab.

5. A self sterilizable free standing frame structure comprising:
   a plurality of modular components according to claim 1, wherein each individual modular component of said plurality of individual modular components interconnect at their respective first or second ends by seamless weld,
   said plurality of individual modular components comprising three or more said individual modular component positioned in vertical manner, each said vertically positioned individual modular component connected at their first end to one or more individual modular component positioned in horizontal manner, three or more horizontally positioned individual modular component interconnected at their first and second ends, forming a self sterilizable free standing frame structure.

6. The self sterilizable free standing frame structure according to claim 5 having no upward slanting surfaces.

7. The self sterilizable free standing frame structure of claim 5 wherein all surfaces are horizontal or downward angled.

8. The plurality of modular components of claim 1, wherein said flat planar material further comprising solid nonporous self-sterilizable material.

9. The plurality of modular components of claim 1, wherein each of said individual modular components has two or more angled bends along and parallel to its said length, each said angle bend along said length need not have the same angle of bend as the other along said length.

* * * * *